Figure 2:
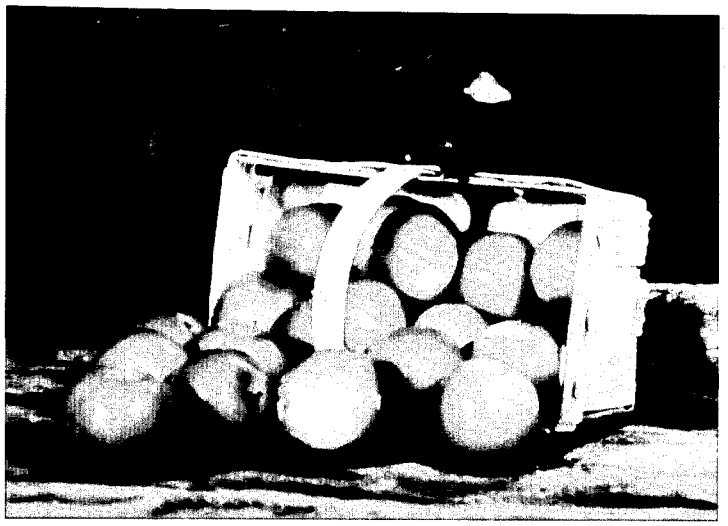

United States Patent [19]

Way et al.

[11] Patent Number: Plant 7,118

[45] Date of Patent: Jan. 23, 1990

[54] APPLE CULTIVAR 'EMPRESS'

[75] Inventors: Roger D. Way, Stanley; Robert C. Lamb, Geneva, both of N.Y.

[73] Assignee: Cornell Research Foundation, Inc., Ithaca, N.Y.

[21] Appl. No.: 281,297

[22] Filed: Dec. 7, 1988

[51] Int. Cl.[4] ..... A01H 5/00

[52] U.S. Cl. ..... Plt./34

[58] Field of Search ..... Plt./34

*Primary Examiner*—Robert E. Bagwill

*Attorney, Agent, or Firm*—Jones, Tullar & Cooper

[57] ABSTRACT

A new and distinct apple cultivar, named 'Empress', (also tested as NY 651), is exceptional for its large fruit size, attractive bright red finish, good yellow flesh color, good eating quality and high fruit yields in the midautumn season.

2 Drawing Sheets

SUMMARY

This invention is a new and distinct apple cultivar known as 'Empress' (also tested as NY 651) which is unique for the combination of its large fruit size, attractive red color, good yellow flesh color, good eating quality and high fruit yields.

ORIGIN

The 'Empress' apple cultivar was developed under project NYG32303 "Apple Breeding" in the Department of Horticultural Sciences, New York State Agricultural Experiment Station, Cornell University, Geneva, N.Y. It was selected from a progeny produced by hybridization in 1969 between 'Jonamac' flowers which were hand-pollinated with pollen from 'Vista Bella'. The original tree, growing on its own roots, bore its first fruits in 1977. Due to its outstanding performance, it was selected for further trial and temporarily assigned the identification, 'NY 651'. By topgrafting and budding in 1978, it was repropagated onto several second-test trees on which its growth and fruiting performances were evaluated for 11 years (1978–1987). It consistently and uniquely performed in a manner superior to other apple cultivars ripening during the same general season. This led to a decision in 1988 to name and introduce it (at the time of filing this application or shortly thereafter) for use by commercial apple growers in large scale apple production. It will be named 'Empress'.

DESCRIPTION OF THE PHOTOGRAPHS

FIG. 1. The blooms of 'Empress' further described below.

FIG. 2. The fruit of 'Empress' further described below.

DESCRIPTION

Trees of 'Empress' are distinctly smaller, i.e., about 70% of the tree size of most apple cultivars. Therefore, they should be either planted closer in the row or propagated on more vigorous rootstocks than other cultivars. Trees resemble the trees of 'Jonamac'. They have spurry branches. Trees grafted on Malling–Merton 106 rootstocks are precocious, beginning to bear crops at 4–5 years of age. 'Empress' is a heavily cropping cultivar. Cropping records of 3 individual trees over a period of 6 years showed that 'Empress' is an annual cropper, without any evidence of a tendency for biennial bearing.

Virus status tests of orchard trees of 'Empress' were conducted by the New York Department of Agriculture and Markets. These tests on woody indicators were negative for chlorotic leaf spot, stem grooving and stem pitting viruses. Thus, 'Empress' is considered to be free of these viruses.

The parents of 'Empress' were selected for their early ripening and their good eating quality. However, 'Empress' does not carry any special resistances to diseases and insects. Thus, 'Empress' orchards will require chemical sprays to control the full range of common pests.

The bloom period of 'Empress' is midseason to late, between 'Delicious' and 'Golden Delicious'. Chromosome counts of 'Empress' made by Cornell University, Department of Horticultural Sciences, showed that 'Empress' is diploid ($2n=34$). Thus, 'Empress' produces viable pollen and therefore, can serve as a pollenizer for other cultivars which bloom during the same general time period.

'Empress' blooms at the time the leaves have already developed to about ⅔ their mature size. Clusters of 4 to 6 flowers emergé from individual flower buds. 'Empress' buds are borne chiefly on spurs from two-year-old or older wood and also occur on terminal buds and on buds developing laterally on the previous year's twigs. Flower size: large (41 to 58 mm in diameter). Pedicels: medium length (30 to 35 mm), thick (1.3 to 1.5 mm); pubescent; light green with a reddish tinge on the side exposed to the sun. Ovary exterior: heavily pubescent. Calyx lobes: long (8.0 to 9.0 mm), medium broad (3.0 to 4.0 mm); lanceolate; entire; the outer surface is heavily pubescent and inner surface has a medium amount of pubescence; calyx lobe tips are reflexed. Petals: large (20 to 25 mm long and 13 to 17 mm wide); elliptic; entire. Petals are shallowly cup-shaped up to one day before they are fully expanded. Fully opened flowers are almost flat. Color of petals: pink at balloon stage but after fully opened they are almost completely white with a faint tinge of pink persisting until petal fall. Petal claws are of medium width (1.0 mm) and are white. Stamens: 18 to 19 in number; large (9 to 12 mm long); shorter than the petals but longer than the pistils; anthers are light yellow; only a small portion of the anthers are aborted. Calyx tube: medium broad (3.0 to 3.5 mm); light green; campanulate. Pistil: medium length (11 mm); length from ovary base to subdivision, 8 mm; pubescent on the portion proximal from subdivision point but glabrous distal from the point of subdivision. Stigma: small with asymmetrical configuration (FIG. 1).

The average date for harvesting 'Empress' fruit at Geneva, N.Y. is August 25, a few days after 'Jerseymac'; a few days before 'Paulared'; and 6 weeks before 'Delicious'. Fruits ripen in late summer during a period in which good, commercially acceptable apple cultivars are lacking. Like most early ripening apple cultivars, 'Empress' fruits ripen unevenly and 2 to 3 pickings are required over a ripening period of a week or more.

Fruit size is medium to large, averaging about 70 mm diameter, but fruit size is smaller when trees are overcropped. Fruit sizes are uncommonly uniform. Fruit shape is round and symmetrical.

Skin color is nearly 100% red. The skin color is comparable to the Red Group 53A (Cardinal Red) of The Royal Horticultural Society Colour Chart published in 1966 by The Royal Horticultural Society, London.

The color pattern is a solid blush, not striped. The skin is covered with a heavy waxy bloom. The over-all appearance is attractive (FIG. 2).

The flesh is semi-firm in texture, juicy, and light yellow in color. The flavor is subacid, vaguely perfumed with very pleasing aromas similar to those of the parent, 'Jonamac'.

Using electrophoresis, isozyme patterns of the 'Empress' apple were analyzed. The phenotype for 'Empress' is approximately as follows: 6-phosphogluconate dehydrogenase-1 (ab); 6-phosphogluconate dehydrogenase-2 (nn); aspartate aminotransferase-1 (cc); aspartate aminotransferase-2 (ac); glucosephosphate isomerase-2 (ac); triosphosphate isomerase-2 (aa); phosphoglucomutase-1 (bb); and phosphoglucomutase-5 (null).

'Empress' is best suited for late summer roadside marketing and probably will not be produced in large quantities for extended storage. The eating quality is very good. This should enhance repeat sales in the marketplace. Fruit should be consumed soon after harvest because it does not remain in a good marketable condition for more than a month when stored at −0.5° C. 'Empress' is useful as a high quality, fully red, attractive, medium- to large-sized, late summer apple for fresh markets. It is not recommended for commercial processing into applesauce or apple slices.

MERITS

The most outstanding features of 'NY 651' are its excellent eating quality, attractive red color, early ripening and heavy and annual cropping. Trees are also precocious in beginning to bear crops at a young age. Trees are less vigorous than many cultivars, thus, making them culturally easier to manage in the orchard.

We claim:

1. The new and distinct apple cultivar herein described and illustrated and identified by the characters enumerated above.

* * * * *

Fruits of 'Empress' (NY 651) apple.